(12) United States Patent
Xie et al.

(10) Patent No.: US 8,940,928 B2
(45) Date of Patent: Jan. 27, 2015

(54) METHOD OF SYNTHESIZING LEVOROTATORY P-HYDROXYPHENYLGLYCINE COMPOUNDS

(75) Inventors: Jianzhong Xie, Changge (CN); Xiubin Guo, Changge (CN); Lixian Zhao, Changge (CN); Chao Liu, Changge (CN)

(73) Assignee: Henan Newland Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 13/994,085

(22) PCT Filed: Feb. 15, 2012

(86) PCT No.: PCT/CN2012/071159
§ 371 (c)(1),
(2), (4) Date: Jun. 13, 2013

(87) PCT Pub. No.: WO2013/120257
PCT Pub. Date: Aug. 22, 2013

(65) Prior Publication Data
US 2014/0350295 A1   Nov. 27, 2014

(51) Int. Cl.
*C07C 229/00* (2006.01)
*C07C 227/18* (2006.01)
*C07F 7/18* (2006.01)
*C07C 231/12* (2006.01)

(52) U.S. Cl.
CPC ............. *C07C 227/18* (2013.01); *C07F 7/1852* (2013.01); *C07C 231/12* (2013.01)
USPC ........................................................ 562/444

(58) Field of Classification Search
None
See application file for complete search history.

(56) References Cited

U.S. PATENT DOCUMENTS

| 3,860,631 A | 1/1975 | Gleason et al. |
| 4,105,690 A | 8/1978 | Christidis et al. |
| 5,336,805 A | 8/1994 | Boesten et al. |

FOREIGN PATENT DOCUMENTS

| CN | 92102863.6 A | 11/1992 |
| CN | 200610025197 | 10/2007 |
| CN | 200810054625 A | 3/2008 |
| CN | 101362703 A | 2/2009 |
| CN | 101613298 A | 12/2009 |
| CN | 102603449 A | 7/2012 |
| EP | 0450684 A1 | 10/1991 |
| EP | 0530879 A1 | 3/1993 |
| JP | 05194337 A | 8/1993 |
| JP | 10279541 A | 10/1998 |
| WO | WO 2009127446 A1 | 10/2009 |

OTHER PUBLICATIONS

Harding et al. (Tetrahedron Letters, 1988, 29(16), 1891).*
International Search Report from corresponding International Application No. PCT/CN2012/071159, dated Nov. 29, 2012.
State of the Art Report dated Dec. 3, 2013 from corresponding Spanish Application No. 201390067.
Skarpos, Hanna, et al., Methyltrifluoropyruvate imines possessing N-oxalyl and N-phosphonoformyl groups—precursors to a variety of α-CF3-α-amino acid, Organic & Biomolecular Chemistry, 2006 年, vol. 4 No. 19, p. 3669-3674.
Ben-Ishai, D., et al., Intra vs intermolecular amidoalkylations of aromatics—a new synthesis of oxindoles, isoquinolones and benzazepinones, Tetrahedron, 1 9 8 0 年, vol. 21 No. 6, p. 569-572.
Ben-Ishai, D., et al., Intra vs intermolecular amidoalkylation of aromatics, Tetrahedron, 1987年, vol. 43 No. 2, p. 439-450.
Onys'ko, P. P., et al., Methyl trifluoropyruvate diethoxyphosphorylimine, Russian Journal of General Chemistry, 2002年, vol. 72 No. 11, p. 1699-1702.
Dirlam, Nancy L., et al., Novel synthesis of the aldose reductase inhibitor sorbinil via amidoalkylation, intramolecular oxazolidin-5-one alkylation and chymotrypsin resolution, Journal of Organic Chemistry, 1987年, vol. 52 No. 16, p. 3587-3591.
Pajkert, Romana, et al., Synthesis of novel α-CF3-trifluoroalanine derivatives containing N-(diethoxyphosphoryl) difluoroacetyl group, Journal of Fluorine Chemistry, 2010年, vol. 131 No. 12, p. 1362-1367.
Xu, Bin, et al., Asymmetric N-H insertion reaction cooperatively catalyzed by rhodium and chiral spiro phosphoric acids, Angewandte Chemie, International Edition , 2011年,vol. 50 No. 48, p. 11483-11486.
Uraguchi, Daisuke, et al. , Chiral bronsted acid-cataly—zed direct mannich reactions via electrophilic activation, Journal of the American Chemical Society, 2004年, vol. 126 No. 17, p. 5356-5357.
Akiyama, Takahiko, et al. , Enantioselective mannich-type reaction catalyzed by a chiral bronsted acid, Angewandte Chemie, International Edition, 2004年, vol. 4 3 No. 12, p. 1566-1568.

(Continued)

*Primary Examiner* — Rosalynd Keys
*Assistant Examiner* — Jennifer C Sawyer
(74) *Attorney, Agent, or Firm* — Wolf, Greenfield & Sacks, P.C.

(57) ABSTRACT

The present invention relates to the field of chemical synthesis, particularly to a method of synthesizing levorotatory p-hydroxyphenylglycine compounds, which eliminates the subsequent processes of resolution, racemization processings, etc., simplifies operational steps; and acids with small organic molecule are chosen as catalyst in the second step, which not only is conducive to the realization of a industrialized production, but also makes the ee value of the end products be 88.1~98.0% by determining the catalyst, the reaction solvent, the reactive substance, the reaction temperature, and the reaction duration; non-aqueous solvent is used in the second step, to avoid the discharging of phenol-containing waste water, thus environmental pollution is reduced.

10 Claims, 1 Drawing Sheet

(56) References Cited

OTHER PUBLICATIONS

Ben-Ishai, D., et al., A new synthesis of N-acyl aromatic α-amino acids—amidoalkylation of aromatic and heterocyclic compounds with glyoxylic acid derivatives, Tetrahedron, 1976, vol. 32 No. 13, p. 1571-1573.

Harding, Kenn E., et al., Acyclic stereoselection in α-amidoalkylation reactions, Tetrahedron Letters, 1988, vol. 29 No. 16, p. 1891-1894.

Qian, Yu, et al., a novel method for synthesizing N-alkoxycarbonyl aryl α-imino esters and their applications in enantioselective transformations, Advanced Synthesis & Catalysis, Jan. 19, 2012, vol. 354 No. 2-3, p. 301-307.

Japanese Office Action mailed Aug. 26, 2014 from corresponding Japanese Application No. 2013-558293.

* cited by examiner

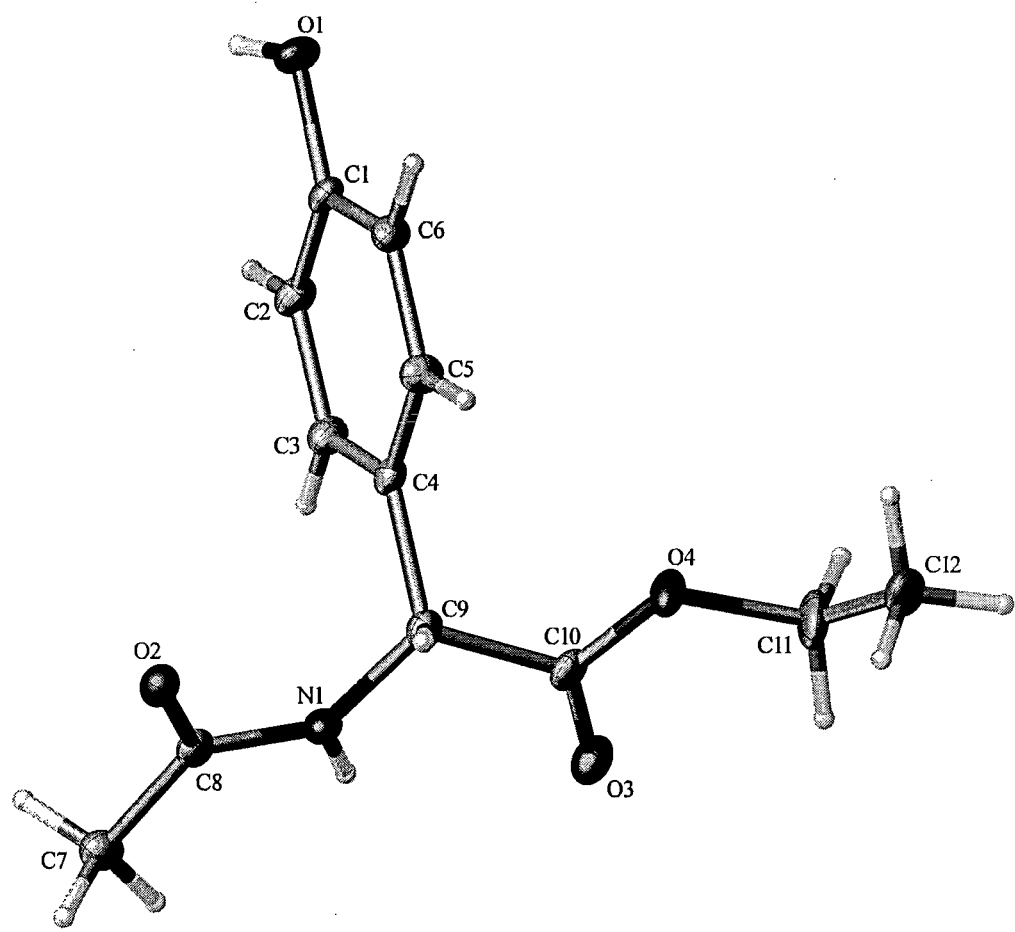

METHOD OF SYNTHESIZING LEVOROTATORY P-HYDROXYPHENYLGLYCINE COMPOUNDS

FIELD OF THE INVENTION

The present invention relates to the field of chemical synthesis, particularly to a method of synthesizing levorotatory p-hydroxyphenylglycine compounds.

BACKGROUND OF THE INVENTION

Levorotary p-hydroxyphenylglycine, which is abbreviated as D-HPG, has a chemical name of D-α-amino p-hydroxyphenylacetic acid, and the structural formula thereof is shown in formula I.

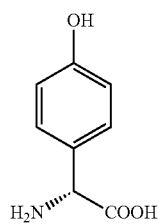

Formula I

Levorotary p-hydroxyphenylglycine is a very important medical intermediate, mainly for the semisynthesis of β-lactam antibiotics. There is no natural product for levorotatory p-hydroxyphenylglycine, which must be obtained by synthetic methods, the synthetic methods thereof are largely divided into two categories: one category is bio-enzymatic catalysis method, which selectively synthesizes D-HPG, such method has a high selectivity and a short synthetic route, however, it is difficult to promote a large-scale industrialized production of this method, due to the biological bacterial culturing problems and that the production process of the raw material p-hydroxyphenylhydantoin will produce a large amount of high concentration phenol-containing waste water; another category is chemical synthesis method, for example: WO2009/127446, EP0530879A1, EP0450684A1, CN200810054625.0, CN92102863.6, and CN200610025197.X disclosed methods for synthesizing and resolving DL-HPG. The chemical synthesis method has advantages of simple production technology, low costs, etc., and currently it is a commonly used method for the industrialized production of D-HPG in China, such method first prepares DL-HPG, and then resolves it to obtain D-HPG. However, L-HPG currently does not have too much application value, parts of which revert to D-HPG after racemization processings, and such method has disadvantages of long technological route, and complicated operation, etc.

SUMMARY OF THE INVENTION

In view of this, the present invention provides a method of synthesizing levorotatory p-hydroxyphenylglycine compounds. This method eliminates the subsequent processes of resolution, racemization processings, etc., simplifies the operational steps, and the ee (enantiomeric excess) value of the end product is high.

To achieve the above purposes of the present invention, the present invention provides the following technical solutions:

The present invention provides a method of synthesizing levorotatory p-hydroxyphenylglycine compounds, comprising the following steps:

step 1: the compound of formula II and the compound of formula III undergo nucleophilic addition reaction in a first solvent, to produce the compound of formula IV; wherein the first solvent is selected from the group consisting of ether solvent, ester solvent, haloalkane solvent, $C_5$~$C_{10}$ hydrocarbon solvent, nitrile solvent, ketone solvent;

As a preference, the first solvent is selected from the group consisting of ether solvent, ester solvent, haloalkane solvent, $C_5$~$C_{10}$ hydrocarbon solvent, nitrile solvent.

As a preference, the ether solvent is selected from the group consisting of diethyl ether, dipropyl ether, 1,4-dioxane, tetrahydrofuran.

As a preference, the ester solvent is selected from the group consisting of ethyl acetate, methyl acetate, propyl acetate, tert-butyl acetate, and ethyl formate.

As a preference, the haloalkane solvent is selected from the group consisting of dichloromethane, trichloromethane, and 1,2-dichloroethane.

As a preference, the $C_5$~$C_{10}$ hydrocarbon solvent is selected from the group consisting of benzene, toluene, and xylene.

As a preference, the nitrile solvent is selected from the group consisting of acetonitrile or propionitrile.

As a preference, the ketone solvent is acetone.

Preferably, the first solvent is preferably one of toluene, methyl acetate, propyl acetate, ethyl acetate, chloroform, dichloromethane, acetone, or a mixture of two or more of them;

step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, $C_5$-$C_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, chiral phosphoric acid, and the achiral acid is selected from the group consisting of methanesulfonic acid, p-toluenesulfonic acid, trifluoromethanesulfonic acid, sulfuric acid, hydrochloric acid;

As a preference, the haloalkane solvent is selected from the group consisting of dichloromethane, trichloromethane, and 1,2-dichloroethane.

As a preference, the $C_5$~$C_{10}$ hydrocarbon solvent is selected from the group consisting of benzene, toluene, and xylene.

As a preference, the nitrile solvent is selected from the group consisting of acetonitrile or propionitrile.

If the chiral acid is used for the catalysis, the compound of formula VI with optical activity will be produced, and if the achiral acid is used as catalyst, a racemic compound of formula VI will be produced.

The chiral phosphoric acid is selected the compound of formula VII, the compound of formula VIII, the compound of formula IX, the compound of formula X, and the compound of formula XI.

Formula VII

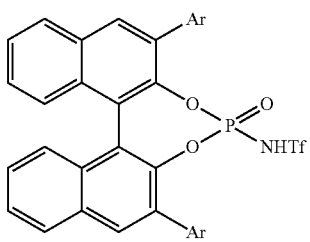

Formula VIII

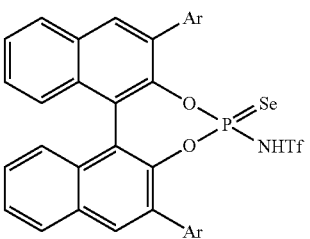

Formula IX

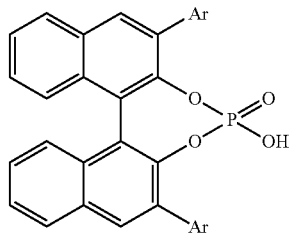

Formula X

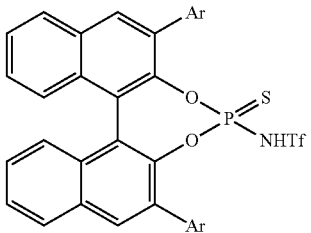

Formula XI

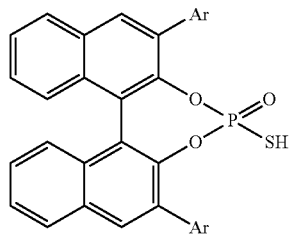

Wherein, Ar is selected from the group consisting of H, Ph, 2,4,6-(i-Pr)$_3$C$_6$H$_2$, 3,5-(CF$_3$)$_2$C$_6$H$_3$, β-Nap, SiPh$_3$, 9-anthryl, 4-biphenyl, 4-NO$_2$—C$_6$H$_4$, 9-phenanthryl, p-MeOC$_6$H$_4$, p-NO$_2$C$_6$H$_4$, i.e., Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl.

Formula II

R$^1$—NH$_2$

Formula III

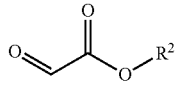

Formula IV

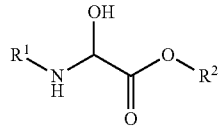

Formula V

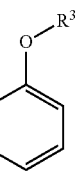

Formula VI

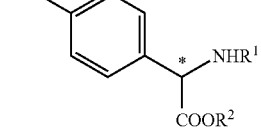

Wherein, R$^1$ is selected from the group consisting of acetyl, benzoyl, tert-butoxycarbonyl, benzyloxycarbonyl, formamido, and pivaloyl; R$^2$ is selected from the group consisting of methyl, ethyl, isopropyl, tert-butyl, and benzyl; and R$^3$ is selected from the group consisting of hydrogen, methyl, trimethylsilyl, tert-butyldimethylsily, and triisopropylsilyl.

As a preference, R$^1$ is selected from the group consisting of acetyl, benzoyl, tert-butoxycarbonyl, and pivaloyl.

As a preference, in step 1, the compound of formula II is selected from the group consisting of acetamide, benzamide, tert-butyl carbamate, benzyl carbamate, and urea.

Preferably, in step 1, the compound of formula II is selected from the group consisting of acetamide, benzamide, tert-butyl carbamate, and benzyl carbamate.

As a preference, in step 1, the molar ratio of the compound of formula II to the compound of formula III is 1:0.5~1:2.1.

Preferably, in step 1, the molar ratio of the compound of formula II to the compound of formula III is 1:1.05.

As a preference, in step 1, the nucleophilic addition reaction is carried out at a temperature of 25~110.6° C. for a period of 0.5~144 h.

Preferably, in step 1, the nucleophilic addition reaction is carried out at a temperature of 28~110.6° C. for a period of 0.5~144 h.

As a preference, in step 2, the molar ratio of the compound of formula IV to the compound of formula V is 1:0.2~1:5.

As a preference, in step 2, the molar ratio of the compound of formula IV or the compound of formula V to the catalyst is 1~200:1.

As a preference, in step 2, the Friedel-Crafts-like reaction is carried out at a temperature of 40~82° C. for a period of 13.5~96 h.

Preferably, in step 2, the Friedel-Crafts-like reaction is carried out at a temperature of 40~80° C. for a period of 23.5~69 h.

The present invention also provides a method of synthesizing levorotatory p-hydroxyphenylglycine, the structure of formula I, comprising the following steps:

step 1: the compound of formula II and the compound of formula III undergo nucleophilic addition reaction in a first solvent, to produce the compound of formula IV; wherein the first solvent is selected from the group consisting of ether solvent, ester solvent, haloalkane solvent, $C_5$~$C_{10}$ hydrocarbon solvent, nitrile solvent, and ketone solvent;

step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, $C_5$-$C_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, and chiral phosphoric acid, and the achiral acid is selected from the group consisting of methanesulfonic acid, p-toluenesulfonic acid, trifluoromethanesulfonic acid, sulfuric acid, and hydrochloric acid;

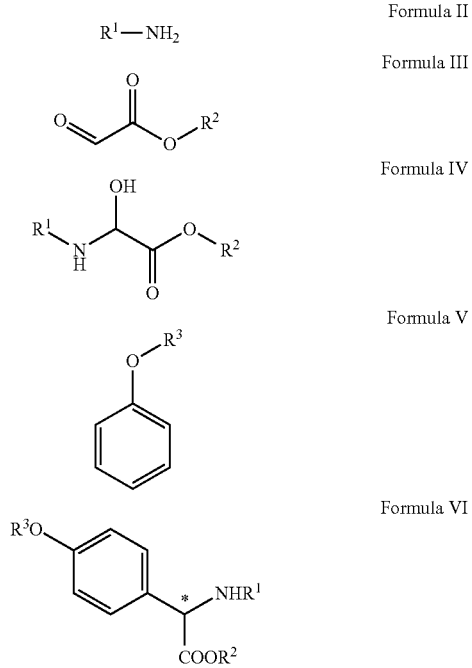

wherein, $R^1$ is selected from the group consisting of acetyl, benzoyl, tert-butoxycarbonyl, benzyloxycarbonyl, formamido, and pivaloyl; $R^2$ is selected from the group consisting of methyl, ethyl, isopropyl, tert-butyl, and benzyl; and $R^3$ is hydrogen;

step 3: in a mixed solution of alcohol and water, or in water, the compound of formula VI undergoes hydrolysis reaction by adjusting the pH value to be <2, then the solution is neutralized with a base to a pH value of 5.2~5.6, to obtain the compound of formula I.

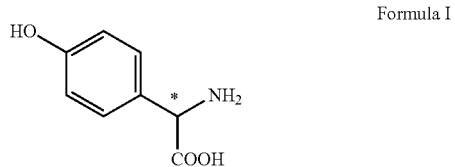 [SMILES: NC(C(=O)O)c1ccc(O)cc1]

As a preference, in step 3, the alcohol solvent is selected from the group consisting of methanol, ethanol, and isopropanol.

As a preference, in step 3, the hydrolysis reaction is carried out at a temperature of 60~100° C.

Preferably, in step 3, the hydrolysis reaction is carried out at a temperature of 60~80° C.

As a preference, in the hydrolysis reaction in step 3, the acid is selected from the group consisting of hydrochloric acid, sulfuric acid, methanesulfonic acid, and trifluoromethanesulfonic acid.

In some examples of the present invention, the concentration of the acid in step 3 is 1 N~12 N.

As a preference, in step 3, the base is selected from the group consisting of sodium hydroxide, sodium bicarbonate, sodium carbonate, potassium hydroxide, aqueous ammonia.

In some examples of the present invention, the concentration of the base in step 3 is 2~12 N.

ee (enantiomeric excess) value, i.e. optical purity, the enantiomeric composition of the compound sample can be described by the term "enantiomeric excess" or "e.e. %", which represents the excess of one enantiomer to the other enantiomer; the synthetic method provided by the present invention eliminates the processes of resolution, racemization processings, etc., in the existing synthetic methods, the optical purity of the levorotatory p-hydroxyphenylglycine compounds prepared can reach 88.1~98.0%.

The present invention provides a method of synthesizing the levorotatory p-hydroxyphenylglycine compounds, which eliminates the subsequent processes of resolution, racemization processings, etc., simplifies operational steps; and acids with small organic molecule are chosen as catalyst in the second step, which not only is conducive to the realization of a industrialized production, but also makes the ee value of the end products be 88.1~98.0% by determining the catalyst, the reaction solvent, the reactive substance, the reaction temperature, and reaction duration; non-aqueous solvent is used in the second step, to avoid the discharging of phenol-containing waste water, thus environmental pollution is reduced.

DESCRIPTION OF THE DRAWINGS

FIG. 1 shows the single crystal figure of D-ethyl-2-acetamido-2-(4-hydroxyphenyl)acetate prepared in Example 1.

DETAILED EMBODIMENTS

The present invention discloses a method of synthesizing the levorotatory p-hydroxyphenylglycine compounds, and a skilled in the art can use the contents herein for reference and achieve by appropriately improving the technological parameters. In particular, all the similar substitutions and alterations are obvious to a skilled in the art, and are all deemed to be within the present invention. The methods and applications of the present invention have been described by preferable examples, and relevant personnel can alter or appropriately change and combine the methods and applications described herein without departing from the content, spirit and scope of the present invention, to realize and apply the techniques of the present invention.

Step 1: the compound of formula II and the compound of formula III undergo nucleophilic addition reaction in a first solvent, to produce the compound of formula IV; wherein the first solvent is selected from the group consisting of ether solvent, ester solvent, haloalkane solvent, $C_5$~$C_{10}$ hydrocarbon solvent, nitrile solvent, and ketone solvent;

As a preference, the first solvent is selected from the group consisting of ether solvent, ester solvent, haloalkane solvent, $C_5$~$C_{10}$ hydrocarbon solvent, and nitrile solvent.

As a preference, the ether solvent is selected from the group consisting of diethyl ether, dipropyl ether, 1,4-dioxane, and tetrahydrofuran.

As a preference, the ester solvent is selected from the group consisting of ethyl acetate, methyl acetate, propyl acetate, tert-butyl acetate, and ethyl formate.

As a preference, the haloalkane solvent is selected from the group consisting of dichloromethane, trichloromethane, and 1,2-dichloroethane.

As a preference, the $C_5$~$C_{10}$ hydrocarbon solvent is selected from the group consisting of benzene, toluene, and xylene.

As a preference, the nitrile solvent is selected from the group consisting of acetonitrile or propionitrile.

As a preference, the ketone solvent is acetone.

Preferably, the first solvent is preferably one of toluene, methyl acetate, propyl acetate, ethyl acetate, chloroform, dichloromethane, acetone, or a mixture of two or more of them;

step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, and $C_5$-$C_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, and chiral phosphoric acid, and the achiral acid is selected from the group consisting of methanesulfonic acid, p-toluenesulfonic acid, trifluoromethanesulfonic acid, sulfuric acid, and hydrochloric acid;

As a preference, the haloalkane solvent is selected from the group consisting of dichloromethane, trichloromethane, and 1,2-dichloroethane.

As a preference, the $C_5$~$C_{10}$ hydrocarbon solvent is selected from the group consisting of benzene, toluene, and xylene.

As a preference, the nitrile solvent is selected from the group consisting of acetonitrile or propionitrile.

If the chiral acid is used for the catalysis, the compound of formula VI with optical activity will be produced, and if the achiral acid is used as catalyst, a racemic compound of formula VI will be produced.

The chiral phosphoric acid is selected from the group consisting of the compound of formula VII, the compound of formula VIII, the compound of formula IX, the compound of formula X, and the compound of formula XI.

Formula VII

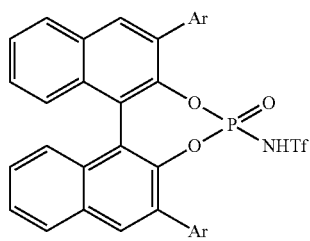

-continued

Formula VIII

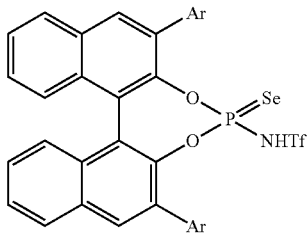

Formula IX

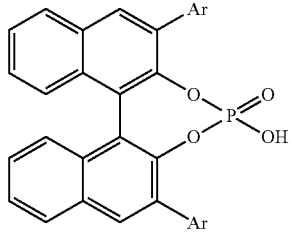

Formula X

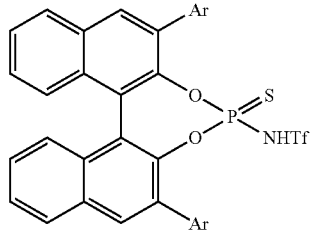

Formula XI

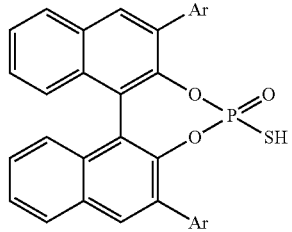

Wherein, Ar is selected from the group consisting of H, Ph, 2,4,6-(i-Pr)$_3$C$_6$H$_2$, 3,5-(CF$_3$)$_2$C$_6$H$_3$, β-Nap, SiPh$_3$, 9-anthryl, 4-biphenyl, 4-NO$_2$—C$_6$H$_4$, 9-phenanthryl, p-MeOC$_6$H$_4$, p-NO$_2$C$_6$H$_4$, i.e., Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl.

Formula II

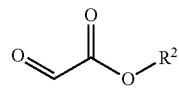

Formula III

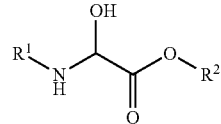

Formula IV

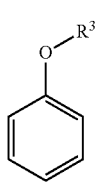

Formula V

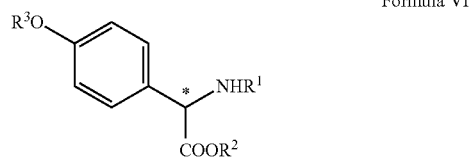

Formula VI

Wherein, $R^1$ is selected from the group consisting of acetyl, benzoyl, tert-butoxycarbonyl, benzyloxycarbonyl, formamido, and pivaloyl; $R^2$ is selected from the group consisting of methyl, ethyl, isopropyl, tert-butyl, and benzyl; and $R^3$ is selected from the group consisting of hydrogen, methyl, trimethylsilyl, tert-butyldimethylsily, and triisopropylsilyl.

As a preference, $R^1$ is selected from the group consisting of acetyl, benzoyl, tert-butoxycarbonyl, and pivaloyl.

As a preference, in step 1, the compound of formula II is selected from the group consisting of acetamide, benzamide, tert-butyl carbamate, benzyl carbamate, and urea.

As a preference, in step 1, the molar ratio of the compound of formula II to the compound of formula III is 1:0.5~1:2.1.

Preferably, in step 1, the molar ratio of the compound of formula II to the compound of formula III is 1:1.05.

As a preference, in step 1, the nucleophilic addition reaction is carried out at a temperature of 25~110.6° C. for a period of 0.5~144 h.

Preferably, in step 1, the nucleophilic addition reaction is carried out at a temperature of 28~110.6° C. for a period of 0.5~144 h.

Specifically, the nucleophilic addition reaction in step 1 may be:

The method of synthesizing ethyl 2-ureido-2-hydroxyacetate is as follows: urea (3.01 g, 50 mmol), ethyl glyoxalate (50% solution in toluene, 11.22 g, 55 mmol), 150 mL acetone are added sequentially into a 250 mL eggplant-shaped flask, reacted at 28° C. for 74 hours, and placed at 0° C. for 12 hours, and the white precipitate is precipitated, filtered, and the filter cake is washed twice with 10 mL acetone, vacuumized for 1 hour, to obtain 3.1 g white solid, and the filtrate is rotary-dried, recrystallized from ethyl acetate, to obtain additional 1.63 g white solid, and the total yield for the two times is 58.4%, melting point: 103-104° C. $^1$H NMR [400 MHz, DMSO]: δ 6.77 (d, J=9.2 Hz, 1H), 6.31 (d, J=6.4 Hz, 1H), 5.78 (s, 2H), 5.34 (dd, J=9.6, 6.8 Hz, 1H), 4.11 (q, J=6.8 Hz 2H), 1.21 (t, J=7.2 Hz, 3H); $^{13}$C NMR [100 MHz, DMSO]: δ 170.3, 157.2, 72.0, 60.6, 14.0.

Specifically, the nucleophilic addition reaction in step 1 may also be:

The method of synthesizing N,N-bis(ethyl-2-hydroxyacetate)urea is as follows: 3.0 g urea (50 mmol), ethyl glyoxalate (50% solution in toluene, 21.42 g, 105 mmol), 150 mL acetone are added sequentially into a 250 mL round bottomed flask, and reacted at 28° C. for 6 days, and the reaction is terminated when plenty of white precipitate is precipitated in the reaction solution. After filtering by suction, the filter cake is vacuum-dried at 30° C. for 12 hours, to obtain 9.18 g white solid, and the yield is 69.5%. $^1$H NMR [400 MHz, DMSO]: δ 7.16-7.10 (m, 2H), 6.53-6.40 (m, 2H), 5.50-5.40 (m, 2H), 4.15-4.10 (m, 4H), 1.23-1.19 (m, 6H); $^{13}$C NMR [100 MHz, DMSO]: δ 170.0, 155.2, 71.9, 60.7, 13.9.

As a preference, in step 2, the molar ratio of the compound of formula IV to the compound of formula V is 1:0.2~1:5.

As a preference, in step 2, the molar ratio of the compound of formula IV or the compound of formula V to the catalyst is 1~200:1.

As a preference, in step 2, the Friedel-Crafts-like reaction is carried out at a temperature of 40~82° C. for a period of 13.5-96 h.

Preferably, in step 2, the Friedel-Crafts-like reaction is carried out at a temperature of 40~80° C. for a period of 23.5-69 h.

The present invention also provides a method of synthesizing levorotatory p-hydroxyphenylglycine with its structure of formula I, comprising the following steps:

step 1: the compound of formula II and the compound of formula III undergo nucleophilic addition reaction in a first solvent, to produce the compound of formula IV; wherein the first solvent is selected from the group consisting of ether solvent, ester solvent, haloalkane solvent, $C_5$~$C_{10}$ hydrocarbon solvent, nitrile solvent, and ketone solvent;

step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, $C_5$-$C_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, and chiral phosphoric acid, and the achiral acid is selected from the group consisting of methanesulfonic acid, p-toluenesulfonic acid, trifluoromethanesulfonic acid, sulfuric acid, and hydrochloric acid;

Formula II $R^1$—$NH_2$

Formula III

Formula IV

Formula V

Formula VI wherein, $R^1$ is selected from the group consisting of acetyl, benzoyl, tert-butoxycarbonyl, benzyloxycarbonyl, formamido, and pivaloyl; $R^2$ is selected from the group consisting of methyl, ethyl, isopropyl, tert-butyl, and benzyl; and $R^3$ is hydrogen;

step 3: in a mixed solution of alcohols and water, or in water, the compound of formula VI undergoes hydrolysis reaction by adjusting the pH value to be <2, then the solution is neutralized with a base to a pH value of 5.2~5.6, to obtain the compound of formula VI; wherein the third solvent is selected from the group consisting of water and alcohol solvent.

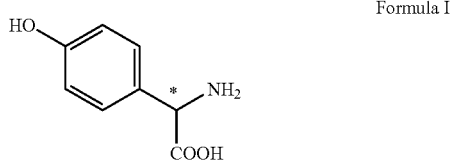 [SMILES: NC(C(=O)O)c1ccc(O)cc1]

Formula I

As a preference, in step 3, the alcohol solvent is selected from the group consisting of methanol, ethanol, and isopropanol.

As a preference, in step 3, the hydrolysis reaction is carried out at a temperature of 60~100° C.

Preferably, in step 3, the hydrolysis reaction is carried out at a temperature of 60~80° C.

As a preference, in the hydrolysis reaction in step 3, the acid is selected from the group consisting of hydrochloric acid, sulfuric acid, methanesulfonic acid, and trifluoromethanesulfonic acid.

In some examples of the present invention, the concentration of the acid in the hydrolysis reaction in step 3 is 1 N~12 N.

As a preference, in step 3, the base is selected from the group consisting of sodium hydroxide, sodium bicarbonate, sodium carbonate, potassium hydroxide, and aqueous ammonia.

In some examples of the present invention, the concentration of the base in step 3 is 2~12 N.

The present invention provides a method of synthesizing the levorotatory p-hydroxyphenylglycine compounds, which eliminates the subsequent processes of resolution, racemization processings, etc., simplifies operational steps; and acids with small organic molecule are chosen as catalyst in the second step, which not only is conducive to the realization of a industrialized production, but also makes the ee value of the end products be 88.1~99.0% by determining the catalyst, the reaction solvent, the reactive substance, the reaction temperature, and the reaction duration; non-aqueous solvent is used in the second step, to avoid the discharging of phenol-containing waste water, thus environmental pollution is reduced.

All the reagents used in the synthetic method provided by the present invention are all commercially available.

The present invention is further illustrated in conjunction with the following examples:

Example 1

Comparative Example

Synthesis of ethyl 2-acetamido-2-hydroxyacetate, the synthetic route is shown as follow:

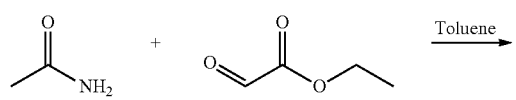

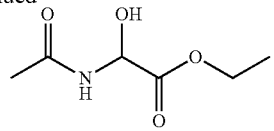

Specific operational steps are as follow:
Acetamide (11.81 g, 0.20 mol), ethyl glyoxalate (50% solution in toluene, 42.84 g, 0.21 mmol), 160 mL toluene were added sequentially into a 500 mL eggplant-shaped flask. And they were reacted at 80° C. for 35 h, then reacted at 60° C. for 27 h, and plenty of white precipitate was precipitated, cooled to room temperature, and filtered by suction, and the filter cake was washed twice with toluene, and vacuum-dried at 40° C. for 24 h. 28.0 g white solid was obtained, the molar yield was 87%, melting point: 88-89° C.

$^1$HNMR [400 MHz, CDCl$_3$]: δ 6.86 (s, 1H), 5.58 (d, J=7.6 Hz, 1H), 4.46 (s, 1H), 4.29 (q, J=7.2 Hz, 2H), 2.05 (s, 3H), 1.33 (t, J=7.2 Hz, 3H); $^{13}$C NMR [100 MHz, CDCl$_3$]; δ 171.3, 169.6, 72.4, 62.8, 23.3, 14.2.

Synthesis of DL-ethyl-2-acetamido-2-(4-hydroxyphenyl) acetate, the synthetic route is shown as follow:

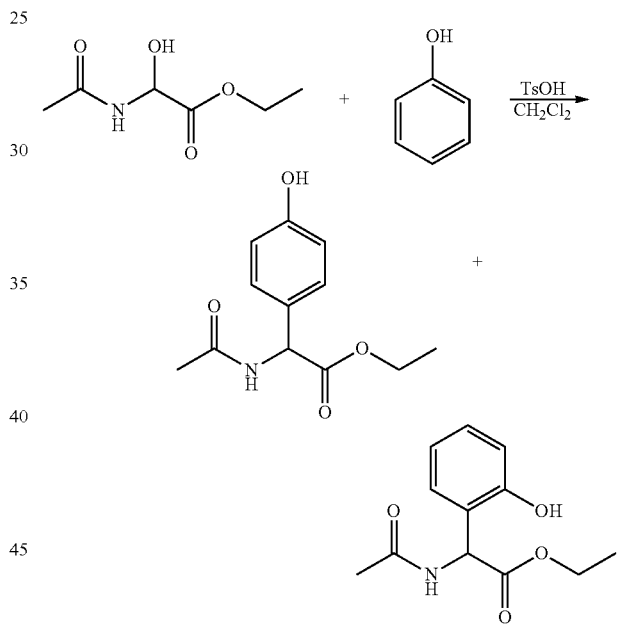

Specific operational steps are as follow:
Ethyl 2-acetamido-2-hydroxyacetate (0.48 g, 3 mmol), phenol (0.33 g, 3.60 mmol), TsOH (0.05 g, 0.30 mmol), 10 mL dichloromethane were added sequentially into a 25 mL eggplant-shaped flask. And they were reacted at room temperature for 38 h, the reaction solution was a colorless transparent liquid, then the reaction was terminated.

It was concentrated, separated by column chromatography, the ortho-product was eluted by petroleum ether/ethyl acetate=1:1, which was a white solid, 59.8 mg, yield 8.4%, melting point: 39-40° C.

$^1$H NMR [400 MHz, CDCl$_3$]: δ 9.05 (s, 1H), 7.20 (td, J=7.6, 1.2 Hz, 1H), 7.12 (d, J=7.2 Hz, 1H), 7.01 (dd, J=7.6, 1.2 Hz, 1H), 6.95 (d, J=8.0 Hz, 1H), 6.84 (t, J=7.6 Hz, 1H), 5.70 (d, J=7.6 Hz, 1H), 4.31-4.16 (m, 2H), 2.02 (s, 3H), 1.20 (t, J=7.2 Hz, 3H); $^{13}$C NMR [100 MHz, CDCl$_3$]: δ 171.5, 171.2, 155.4, 130.4, 128.0, 124.0, 120.7, 118.6, 62.4, 52.5, 22.8, 14.1.

Para-product was eluted by petroleum ether/ethyl acetate=1:2, which was a white solid, 60 mg, yield 8.4%, melting point: 119-121° C.

$^1$H NMR [400 MHz, CDCl$_3$]: δ 7.12 (d, J=8.4 Hz, 2H), 6.93 (d, J=7.2 Hz, 1H), 6.72 (d, J=8.8 Hz, 2H), 5.42 (d, J=6.8 Hz, 1H), 4.29-4.06 (m, 2H), 2.00 (s, 1H), 1.17 (t, J=7.2 Hz, 3H); $^{13}$C NMR [100 MHz, CDCl$_3$]: δ 171.5, 170.8, 157.2, 128.7, 127.4, 116.1, 62.1, 56.5, 23.0, 14.1.

The synthetic method provided by the present invention:
Synthesis of ethyl 2-acetamido-2-hydroxyacetate, the synthetic route is shown as follows:

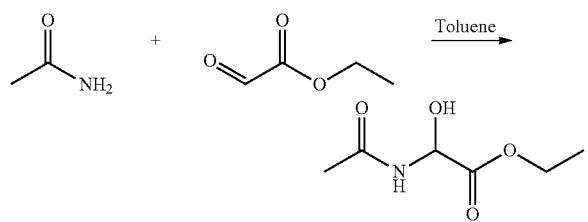

Specific operational steps are as follows:
Acetamide (11.81 g, 0.20 mol), ethyl glyoxalate (50% solution in toluene, 42.84 g, 0.21 mmol), 160 mL toluene were added sequentially into a 500 mL eggplant-shaped flask. And they were reacted at 80° C. for 35 h, then reacted at 60° C. for 27 h, and plenty of white precipitate was precipitated, cooled to room temperature, and filtered by suction, and the filter cake was washed twice with toluene, and vacuum-dried at 40° C. for 24 h. 28.0 g white solid was obtained, the molar yield was 87%, melting point: 88-89° C.

$^1$HNMR [400 MHz, CDCl$_3$]: δ 6.86 (s, 1H), 5.58 (d, J=7.6 Hz, 1H), 4.46 (s, 1H), 4.29 (q, J=7.2 Hz, 2H), 2.05 (s, 3H), 1.33 (t, J=7.2 Hz, 3H); $^{13}$C NMR [100 MHz, CDCl$_3$]; δ 171.3, 169.6, 72.4, 62.8, 23.3, 14.2.

Synthesis of D-ethyl-2-acetamido-2-(4-hydroxyphenyl) acetate, the synthesis route is shown as follows:

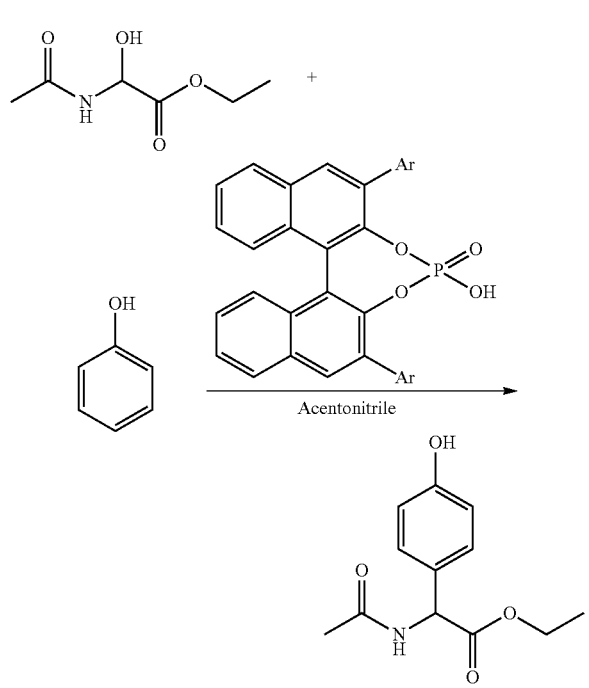

Specific operational steps are as follows:
Ethyl 2-acetamido-2-hydroxyacetate (1.932 g, 12 mmol), 0.1 mmol catalyst chiral phosphoric acid (wherein Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), phenol (0.94 g, 10 mmol), 50 mL acetonitrile were added sequentially into a 100 mL three-necked bottle equipped with a constant pressure dropping funnel and a thermometer, and the reaction solution was reacted at 81° C. for 34 hours, then the reaction was terminated. 23 mL water was added, and stirred at room temperature for 4 hours, and the catalyst was filtered out with a recovery rate of 88.2%. The filtrate was rotary-dried, loaded and eluted by a silica gel column after dissolving the sample with dichloromethane, the catalyst and phenol were eluted by petroleum ether:ethyl acetate:glacial acetic acid=600:200:16, and the ortho- and para-products were eluted by petroleum ether:ethyl acetate=3250:3250. 1.47 g para-product, yield 62%, melting point: 147-148° C., ee=90%. (HPLC conditions: chiralPAK AD-H 5 μm, 4.6×250 mm chromatographic column, n-hexane/isopropanol=9:1 was the mobile phase, the flow rate was 1.0 mL/min, the maximum absorption wavelength was 229 nm).

$^1$H NMR [400 MHz, CDCl$_3$]: δ 7.17 (d, J=8.4 Hz, 2H), 6.73 (d, J=8.4 Hz, 2H), 6.58 (d, J=6.4 Hz, 1H), 5.47 (d, J=6.8 Hz, 1H), 4.27-4.10 (m, 2H), 2.04 (s, 3H), 1.21 (t, J=7.2 Hz, 3H); $^{13}$C NMR [100 MHz, CDCl$_3$]: δ 171.4, 170.0, 156.5, 128.7, 128.4, 116.1, 62.2, 56.3, 23.4, 14.2.

The single crystal figure of D-ethyl-2-acetamido-2-(4-hydroxy phenyl)acetate is shown in FIG. 1.

The D-ethyl-2-acetamido-2-(4-hydroxyphenyl)acetate obtained in the method provided by the present invention was prepared into levorotatory p-hydroxyphenylglycine hydrochloride, the synthetic route is shown as follows:

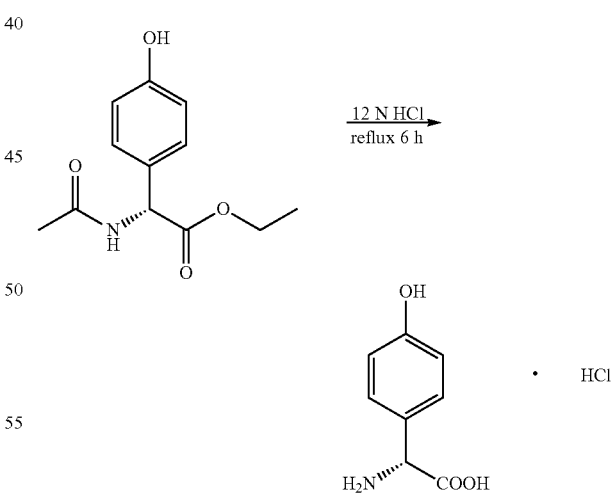

Specific operational steps are as follows:
0.1 g D-ethyl-2-acetamido-2-(4-hydroxyphenyl)acetate, 2 mL concentrated hydrochloric acid (12 N hydrochloric acid) were sequentially added into a 10 mL schlenk tube, and started to stir, and refluxed at 100° C. for 6.5 h, then the reaction was terminated, the reaction solution was rotary-dried to obtain 81.1 mg pale yellow solid, the yield was 95.1%. $[α]_D^{20}$=−90° (c=1.0, water).

¹H NMR [400 MHz, D₂O]: δ7.30 (d, J=8.4 Hz, 2H), 6.90 (d, J=8.8 Hz, 2H), 5.07 (s, 1H); ¹³C NMR [100 MHz, D₂O]: δ171.1, 157.0, 129.8, 123.2, 116.3, 56.1.

Example 2

Comparative Example

Synthesis of ethyl 2-benzamido-hydroxyacetate, the synthetic route is shown as follow:

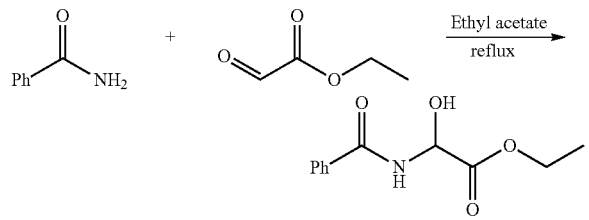

Specific operational steps are as follows:

Benzamide (7.21 g, 60 mmol), ethyl glyoxalate (50% solution in toluene, 10.32 g, 50 mmol), 55 mL ethyl acetate were sequentially added into a 250 mL eggplant-shaped flask, and started to stir, and started to heat, when the temperature reached 53° C., the reaction solution changed from a suspension into a colorless transparent liquid. Continued to heat, and reacted under reflux at 77.06° C. for 13 h, then stopped heating and stirred at room temperature overnight, and white precipitate was precipitated, filtered by suction, and the filter cake was soaked and washed with 3×5 mL ethyl acetate, and vacuum-dried at 40° C., to obtain 7.08 g white solid, the yield was 63.5%, melting temperature: 114-115° C.

¹H NMR [400 MHz, CDCl₃]: δ7.81 (d, J=7.6 Hz, 2H), 7.58-7.48 (m, 2H), 7.44 (t, J=7.6 Hz, 2H), 5.81 (d, J=7.2 Hz, 1H), 4.57 (s, 1H), 4.32 (q, J=7.2 Hz, 2H), 1.34 (t, J=7.2 Hz, 3H); ¹³C NMR [100 MHz, CDCl₃]: δ 169.7, 168.2, 133.1, 132.6, 128.9, 127.5, 72.9, 62.9, 14.3.

Synthesis of DL-ethyl-2-benzamido-2-(4-hydroxyphenyl)acetate, the synthetic route is shown as follows:

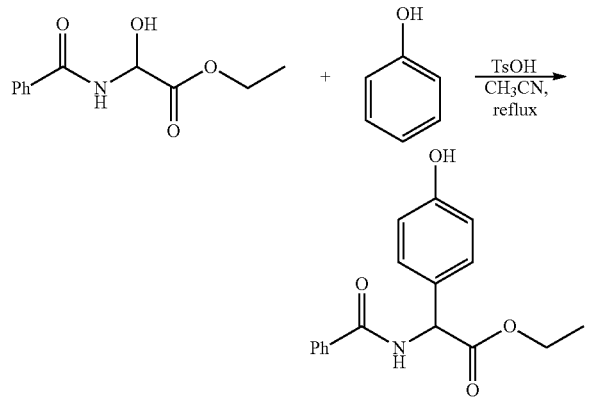

Specific operational steps are as follows:

Ethyl 2-benzamido-2-hydroxyacetate (2.23 g, 10 mmol), TsOH (0.35 g, 2 mmol), PhOH (1.14 g, 12 mmol), 10 mL CH₃CN were sequentially added into a 50 mL eggplant-shaped flask, and started to stir, and started to heat, when the temperature reached 48° C., the reaction solution changed from a suspension into a colorless transparent liquid. Continued to heat, and the reaction was terminated after refluxing for 13.5 h. Separated by column chromatography, and the para-product was eluted by petroleum ether/ethyl acetate=3:1, which was a white solid, 0.66 g, yield 22.2%, melting point: 156-157° C.

¹H NMR [400 MHz, MeOD]: δ 8.78 (d, J=6.0 Hz, 1H), 7.84 (d, J=7.2 Hz, 2H), 7.52 (t, J=7.6 Hz, 1H), 7.44 (t, J=7.6 Hz, 2H), 7.29 (d, J=8.8 Hz, 2H), 6.81 (d, J=8.8 Hz, 2H), 5.60-5.50 (m, 1H), 4.24-4.15 (m, 2H), 1.22 (t, J=7.2 Hz, 3H); ¹³C NMR [100 MHz, MeOD]: δ 172.7, 170.2, 158.9, 135.1, 132.8, 130.4, 129.5, 128.6, 127.9, 116.6, 62.6, 58.7, 14.4.

The synthetic method provided by the present invention:

Synthesis of ethyl 2-benzamido-2-hydroxyacetate, the synthetic route is shown as follows:

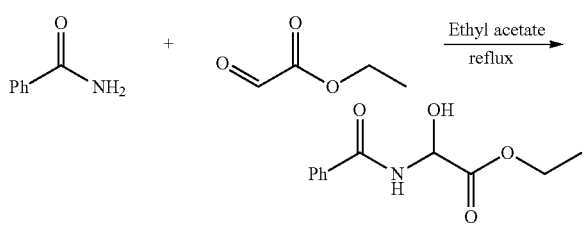

Specific operational steps are as follows:

Benzamide (7.21 g, 60 mmol), ethyl glyoxalate (50% solution in toluene, 10.32 g, 50 mmol), 55 mL ethyl acetate were sequentially added into a 250 mL eggplant-shaped flask, and started to stir, and started to heat, when the temperature reached 53° C., the reaction solution changed from a suspension into a colorless transparent liquid. Continued to heat, and reacted under reflux at 77.06° C. for 13 h, then stopped heating and stirred at room temperature overnight, white precipitate was precipitated, filtered by suction, and the filter cake was soaked and washed with 3×5 mL ethyl acetate, and vacuum-dried at 40° C., to obtain 7.08 g white solid, the yield was 63.5%, melting temperature: 114-115° C.

¹H NMR [400 MHz, CDCl₃]: δ7.81 (d, J=7.6 Hz, 2H), 7.58-7.48 (m, 2H), 7.44 (t, J=7.6 Hz, 2H), 5.81 (d, J=7.2 Hz, 1H), 4.57 (s, 1H), 4.32 (q, J=7.2 Hz, 2H), 1.34 (t, J=7.2 Hz, 3H); ¹³C NMR [100 MHz, CDCl₃]: δ 169.7, 168.2, 133.1, 132.6, 128.9, 127.5, 72.9, 62.9, 14.3.

Synthesis of D-ethyl-2-benzamido-2-(4-hydroxyphenyl)acetate, the synthetic route is shown as follows:

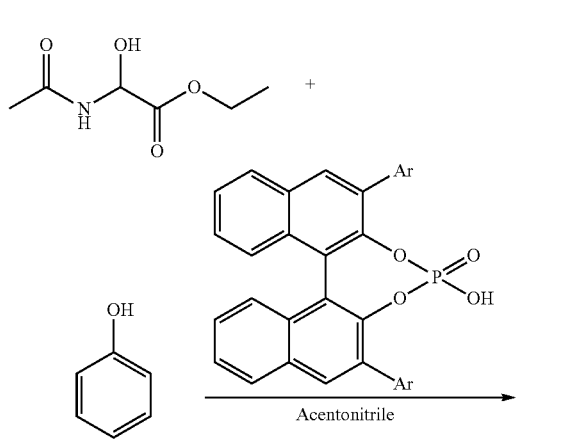

-continued

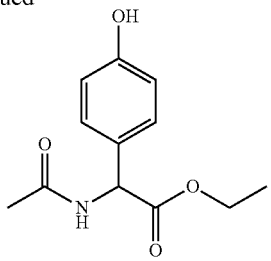

Specific operational steps are as follows:

Ethyl 2-benzamido-2-acetate (0.223 g, 1 mmol), chiral phosphoric acid (0.1 mmol) (wherein, Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), PhOH (0.112 g, 1.2 mmol), 2 mL $CH_3CN$ were sequentially added into a 10 mL schlenk tube, and started to stir, and started to heat, and the reaction was terminated after refluxing at 81.6° C. for 23.5 h. 1.2 mL water was added, and the catalyst was precipitated, filtered, and the filtrate was rotary-dried, and separated by column chromatography, phenol and the rest of catalyst were eluted by petroleum ether/ethyl acetate=5:1, and para-product was eluted by petroleum ether/ethyl acetate=3:1, which was a white solid, 40 mg, yield 13.4%. ee=88.1% (HPLC conditions: ChiralCEL OD-H 5 μm, 4.6×250 mm chromatographic column, n-hexane/isopropanol=90:10 was the mobile phase, the flow rate was 1.0 mL/min, and the maximum absorption wavelength was 229 nm).

$^1$H NMR [400 MHz, $CDCl_3$]: δ 7.83 (d, J=6.8 Hz, 2H), 7.62-7.52 (m, 1H), 7.44 (t, J=7.6 Hz, 2H), 7.23 (d, J=8.8 Hz, 2H), 6.70 (d, J=8.4 Hz, 2H), 6.41 (s, 1H), 5.64 (d, J=6.8 Hz, 1H), 4.32-4.13 (m, 2H), 1.23 (t, J=7.2 Hz, 3H); $^{13}$C NMR [100 MHz, $CDCl_3$]: δ 171.5, 167.1, 156.7, 133.7, 132.2, 128.9, 128.7, 128.2, 127.4, 116.2, 62.3, 56.7, 14.2.

Example 3

Comparative Example

Synthesis of ethyl 2-tert-butoxycarbonylamino-2-hydroxyacetate, the synthetic route is shown as follows:

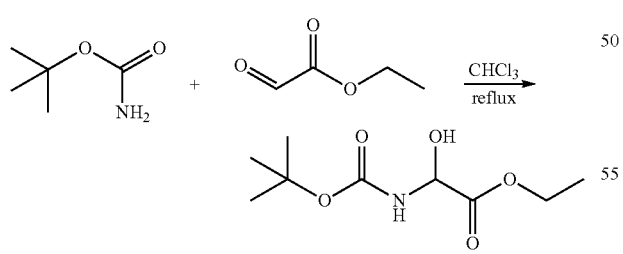

Specific operational steps are as follows:

Boc-$NH_2$ (6.15 g, 52.5 mmol), ethyl glyoxalate (50% solution in toluene, 10.29 g, 50 mmol), 15 mL $CHCl_3$ were sequentially added into a 50 mL eggplant-shaped flask, and started to stir, the reaction solution was a colorless transparent liquid, and reacted under reflux at 61.70° C. for 60 h, then the reaction was terminated. Separated by column chromatography, and the target product was eluted by petroleum ether/ethyl acetate=8:1, which was a white solid, 8.02 g, yield 73.2%, melting point: 54-56° C.

$^1$HNMR [400 MHz, $CDCl_3$]: δ 5.89 (d, J=8.0 Hz, 1H), 5.39 (s, 1H), 4.38 (s, 1H), 4.30-4.21 (m, 2H), 1.43 (s, 9H), 1.30 (t, J=7.2 Hz, 3H); $^{13}$C NMR [100 MHz, $CDCl_3$]: δ 169.8, 155.1, 81.1, 73.6, 62.6, 28.4, 14.2.

Synthesis of DL-ethyl-2-tert-butoxycarbonylamino-2-(4-hydroxy phenyl)acetate, the synthetic route is shown as follows:

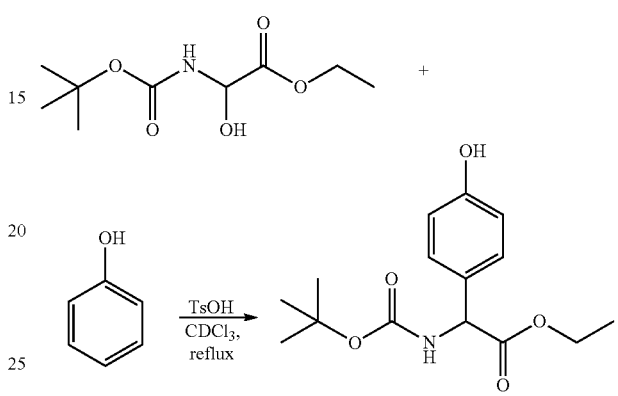

Specific steps are as follows:

Ethyl 2-tert-butoxycarbonylamino-2-hydroxyacetate (423.3 mg, 1.93 mmol), TsOH (33.9 mg, 0.19 mmol), PhOH (218.0 mg, 2.32 mmol), 2.5 mL $CHCl_3$ were sequentially added into a 25 mL eggplant-shaped flask, and reacted under reflux for 11 h, then the reaction was terminated. Separated by column chromatography, and the para-product was eluted by petroleum/ethyl acetate=6:1, which was an off-white solid, 85.4 mg, yield 15%.

$^1$H NMR [400 MHz, $CDCl_3$]: δ 7.12 (d, J=8.0 Hz, 2H), 6.70 (d, J=7.6 Hz, 2H), 5.66 (d, J=6.4 Hz, 1H), 5.17 (d, J=6.8 Hz, 1H), 4.16-4.07 (m, 2H), 1.42 (s, 9H), 1.16 (t, J=6.8 Hz, 3H); $^{13}$C NMR [100 MHz, $CDCl_3$]: δ 171.7, 156.8, 155.3, 128.5, 128.1, 116.0, 80.7, 62.0, 57.4, 28.4, 14.1.

The synthetic method provided by the present invention:

Synthesis of ethyl 2-tert-butoxycarbonylamino-2-hydroxyacetate, the synthetic route is shown as follows:

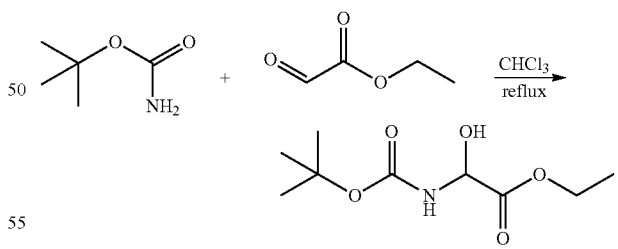

Specific operational steps are as follows:

Boc-$NH_2$ (6.15 g, 52.5 mmol), ethyl glyoxalate (50% solution in toluene, 10.29 g, 50 mmol), 15 mL $CHCl_3$ were sequentially added into a 50 mL eggplant-shaped flask, and started to stir, the reaction solution was a colorless transparent liquid, and reacted under reflux at 61.70° C. for 60 h, then the reaction was terminated. Separated by column chromatography, and the target product was eluted by petroleum ether/ethyl acetate=8:1, which was a white solid, 8.02 g, yield 73.2%, melting point: 54-56° C.

¹HNMR [400 MHz, CDCl₃]: δ 5.89 (d, J=8 Hz, 1H), 5.39 (s, 1H), 4.38 (s, 1H), 4.30-4.21 (m, 2H), 1.43 (s, 9H), 1.30 (t, J=7.2 Hz, 3H); ¹³C NMR [100 MHz, CDCl₃]: δ 169.8, 155.1, 81.1, 73.6, 62.6, 28.4, 14.2.

Synthesis of D-ethyl-2-tert-butoxycarbonylamino-2-(4-hydroxy phenyl)acetate, the synthetic route is shown as follow:

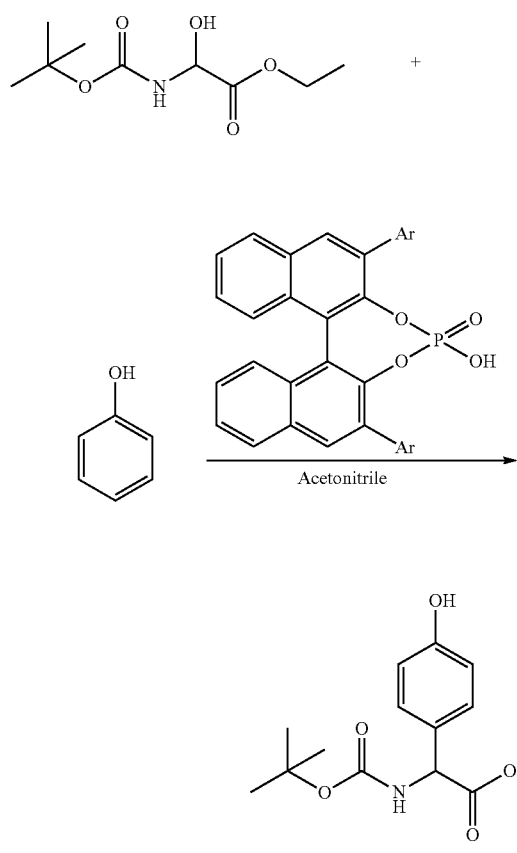

Specific operational steps are as follows:

Ethyl 2-tert-butoxycarbonylamino-2-hydroxyacetate (0.44 g, 2 mmol), 0.2 mmol chiral phosphoric acid (Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), phenol (0.23 g, 2.4 mmol), 10 mL acetonitrile were sequentially added into a 25 mL two-necked bottle, and reacted under reflux at 81.6° C. for 12 hours and 15 minutes, then the reaction was terminated. Separated by column chromatography, and 0.10 g para-product was eluted by petroleum ether/ethyl acetate/glacial acetic acid=70:10:5, which was an off-white solid, yield 16.9%. ee=93.6% (HPLC conditions: ChiralCEL OD-H 5 μm, 4.6×250 mm chromatographic column, n-hexane/isopropanol=92.5:7.5 was the mobile phase, the flow rate was 0.5 mL/min, and the maximum absorption wavelength was 229 nm).

¹H NMR [400 MHz, CDCl₃]: δ 7.14 (d, J=7.6 Hz, 2H), 6.72 (d, J=8.4 Hz, 2H), 5.62 (d, J=6 Hz, 1H), 5.18 (d, J=6.8 Hz, 1H), 4.20-4.09 (m, 2H), 1.43 (s, 9H), 1.18 (t, J=6.8 Hz, 3H); ¹³C NMR [100 MHz, CDCl₃]: δ 171.8, 156.6, 155.4, 128.6, 128.3, 116.0, 80.7, 62.0, 57.4, 28.5, 14.2.

Example 4

Synthesis of phenoxytrimethylsilane, the synthetic route is shown as follows:

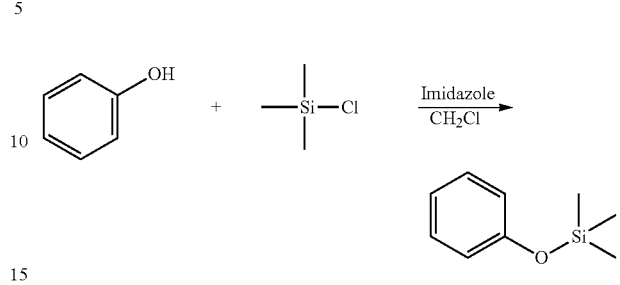

Specific operational steps are as follows:

1.88 g phenol (20 mmol), 1.63 g imidazole (24 mmol), 30 mL dichloromethane, 3.1 mL trimethylchlorosilane (24 mmol) were sequentially added into a 100 mL eggplant-shaped flask, and reacted under reflux at 40° C. for 46 hours, then the reaction was terminated. The reaction solution was rotary-dried, and eluted by a silica gel column, 0.56 g product was eluted with pure petroleum ether, which was a colorless oily liquid, yield 17%.

¹HNMR [400 MHz, CDCl₃]:67.31-7.27 (m, 2H), 7.02 (t, J=7.6 Hz, 1H), 6.92 (d, J=8.0 Hz, 2H), 0.34 (s, 9H); ¹³C NMR [100 MHz, CDCl₃]: δ 155.4, 129.6, 121.6, 120.3, 0.4.

Synthesis of ethyl 2-acetamido-2-hydroxyacetate, the synthetic route is shown as follows:

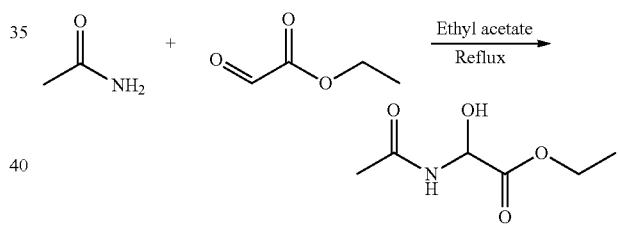

Specific operational steps are as follows:

Acetamide (1.47 g, 25 mmol), ethyl glyoxalate (50% solution in toluene, 5.35 g, 26.25 mmol), 20 mL ethyl acetate were added sequentially into a 50 mL eggplant-shaped flask. And they were reacted under reflux at 77.06° C. for 45 h, then cooled to a temperature of 25° C., plenty of white precipitate was precipitated, filtered by suction, and vacuum-dried at 45° C. for 11 h. 2.48 g white solid was obtained, and the molar yield was 62%.

¹HNMR [400 MHz, CDCl₃]: δ 6.99 (d, J=6.4 Hz, 1H), 5.65-5.50 (m, 1H), 4.69 (d, J=5.6 Hz, 1H), 4.27 (q, J=7.2 Hz, 2H), 2.04 (s, 3H), 1.31 (t, J=7.2 Hz, 3H).

Synthesis of D-ethyl-2-acetamido-2-(4-hydroxyphenyl)acetate, the synthetic route is shown as follows:

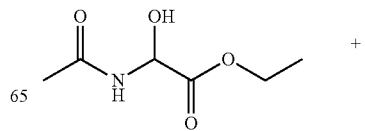

-continued

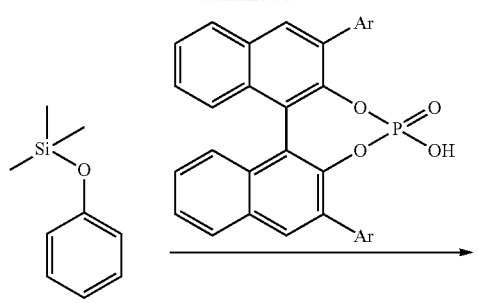

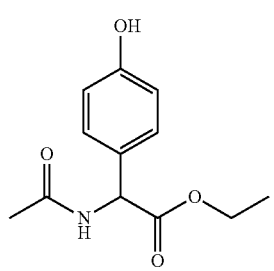

Specific operational steps are as follows:

16.1 mg ethyl 2-acetamido-2-hydroxyacetate (0.1 mmol), 0.01 mmol catalyst chiral phosphoric acid (Ar is selected from the group consisting of hydrogen, phenyl, 2,4,6-triisopropylphenyl, 3,5-bis(trifluoromethyl)phenyl, fi-naphthyl, triphenylsilyl, 9-anthryl, 4-biphenylyl, 4-nitrophenyl, 9-phenanthryl, 4-methoxyphenyl, and 4-nitrophenyl), 20 mg phenoxytrimethylsilane (0.12 mmol), 0.6 mL CD₃CN were sequentially add into an NMR tube with Φ=5 mm, I=180 mm, and reacted at 60° C. for 29 hours, then reacted at 80° C. for 19 hours, then the reaction was terminated. The reaction solution was rotary-dried, separated by silica gel column, and 5 mg product was eluted with petroleum ether:ethyl acetate=4:5, yield 21.1%. ee=97.4%. (HPLC conditions: chiralPAK AD-H 5 μm, 4.6×250 mm chromatographic column, n-hexane/isopropanol=9:1 was the mobile phase, the flow rate was 1.0 mL/min, and the maximum absorption wavelength was 229 nm).

¹H NMR [400 MHz, CDCl₃]: δ 7.17 (d, J=8.4 Hz, 2H), 6.73 (d, J=8.8 Hz, 2H), 6.56 (d, J=6.4 Hz, 1H), 6.44 (s, 1H), 5.46 (d, J=6.8 Hz, 1H), 4.32-4.10 (m, 2H), 2.04 (s, 3H), 1.21 (t, J=7.2 Hz, 3H).

Synthesis of levorotatory p-hydroxyphenylglycine hydrochloride, the synthetic route is shown as follows:

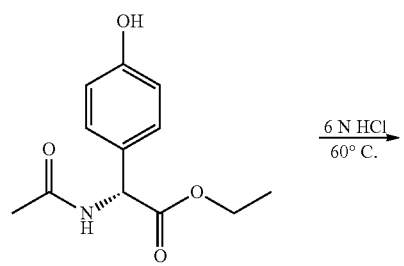

-continued

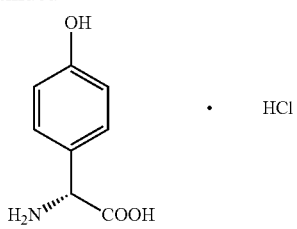

Specific operational steps are as follows:

99.3 mg D-ethyl-2-acetamido-2-(4-hydroxyphenyl)acetate (0.42 mmol), 2 mL 6 N hydrochloric acid were sequentially added into a 10 mL schlenk tube, and started to stir, reacted at 60° C. for 45 h, then the reaction was terminated, the reaction solution was rotary-dried, to obtain 66.8 mg white solid, yield 95%. [α]$_D^{20}$=−99.7° (c=1.0, water).

¹H NMR [400 MHz, D₂O]: δ7.35 (d, J=8.8 Hz, 2H), 6.96 (d, J=8.8 Hz, 2H), 5.09 (s, 1H); ¹³C NMR [100 MHz, D₂O]: δ171.3, 157.1, 129.8, 123.4, 116.3, 56.2.

Example 5

Synthesis of ethyl 2-acetamido-2-hydroxyacetate, the synthetic route is shown as follows:

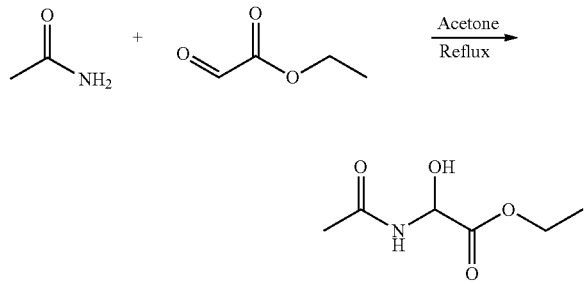

Specific operational steps are as follows:

Acetamide (1.47 g, 25 mmol), ethyl glyoxalate (50% solution in toluene, 5.35 g, 26.25 mmol), 20 mL acetone were sequentially added into a 50 mL eggplant-shaped flask. They were reacted under reflux at 56.2° C. for 45 h, and then cooled to a temperature 25° C., and plenty of precipitate was precipitated, filtered by suction, vacuum-dried at 45° C. for 11 h. 1.76 g white solid was obtained, and the molar yield was 43.82%.

¹HNMR [400 MHz, CDCl₃]: δ 6.82 (s, 1H), 5.61-5.55 (m, 1H), 4.40-4.20 (m, 3H), 2.05 (s, 3H), 1.33 (t, J=7.2 Hz, 3H).

Synthesis of D-ethyl-2-acetamido-2-(4-hydroxyphenyl) acetate, the synthetic route is shown as follows:

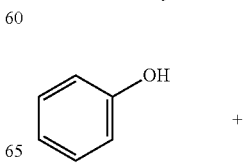 +

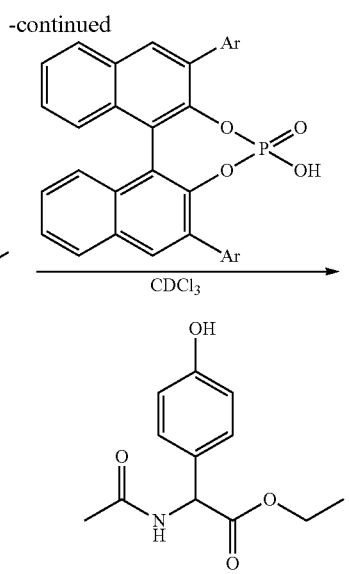

Specific operational steps are as follows:

161 mg ethyl 2-acetamido-2-hydroxyacetate (1 mmol), 0.01 mmol catalyst chiral phosphoric acid (Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), 423 mg phenol (4.5 mmol), 6 mL CDCl₃ were added sequentially into a 25 mL eggplant-shaped flask, and reacted at 50° C. for 42.5 hours, then reacted at 62° C. for 46.5 hours, then the reaction was terminated. The reaction solution was rotary-dried, the product was separated by silica gel column, and 16 mg para-product was eluted with petroleum ether:ethyl acetate:methanol=25:25:1, yield 7%. ee=93.1%. (HPLC conditions: chiralPAK AD-H 5 m, 4.6×250 mm chromatographic column, n-hexane/isopropanol=9:1 was the mobile phase, the flow rate was 1.0 mL/min, the maximum absorption wavelength was 229 nm).

¹H NMR [400 MHz, CDCl₃]: δ 7.15 (d, J=7.6 Hz, 2H), 6.71 (d, J=8.4 Hz, 2H), 6.59 (s, 1H), 5.46 (d, J=6.8 Hz, 1H), 4.29-4.06 (m, 2H), 2.04 (s, 3H), 1.21 (t, J=7.2 Hz, 3H).

Synthesis of levorotatory p-hydroxyphenylglycine hydrochloride, the synthetic route is shown as follows:

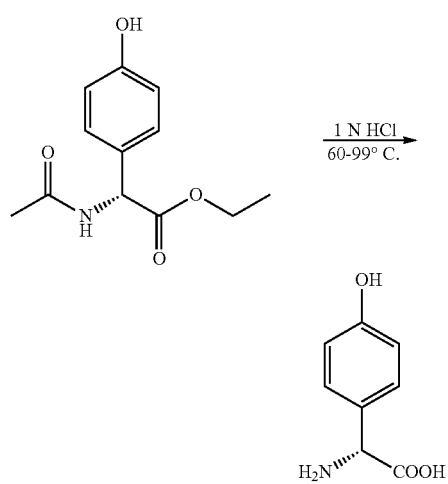

Specific operational steps are as follows:

99.6 mg D-ethyl-2-acetamido-2-(4-hydroxyphenyl)acetate (0.42 mmol), 2 mL 1 N hydrochloric acid were sequentially added into a 10 mL schlenk tube, and started to stir, reacted at 60° C. for 45 h, and heated to 80° C. and reacted for 13.5 h, then heated to 99° C. and reacted for 11 h, then the reaction was terminated, the reaction solution was rotary-dried, to obtain 70.0 mg white solid, yield 99%. $[\alpha]_D^{20}=-85°$ (c=1.0, water).

¹H NMR [400 MHz, D₂O]: δ7.34 (d, J=8.8 Hz, 2H), 6.95 (d, J=8.4 Hz, 2H), 5.06 (s, 1H).

Example 6

Synthesis of ethyl 2-acetamido-2-hydroxyacetate, the synthetic route is shown as follows:

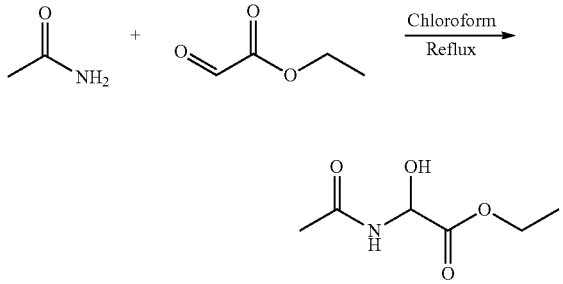

Specific operational steps are as follows:

Acetamide (1.47 g, 25 mmol), ethyl glyoxalate (50% solution in toluene, 5.23 g, 26.25 mmol), 20 mL chloroform were added sequentially into a 50 mL eggplant-shaped flask. And they were reacted at 61.7° C. for 45 h, cooled to a temperature of 25° C., plenty of white precipitate was precipitated, filtered by suction, and vacuum-dried at 45° C. for 11 h. 2.00 g white solid was obtained, and the molar yield was 50%.

¹HNMR [400 MHz, CDCl₃]: δ 6.84 (s, 1H), 5.65-5.50 (m, 1H), 4.38 (d, J=5.6 Hz, 1H), 4.29 (q, J=7.2 Hz, 2H), 2.05 (s, 3H), 1.33 (t, J=7.2 Hz, 3H).

Synthesis of D-ethyl-2-acetamido-2-(4-hydroxyphenyl)acetate, the synthetic route is shown as follows:

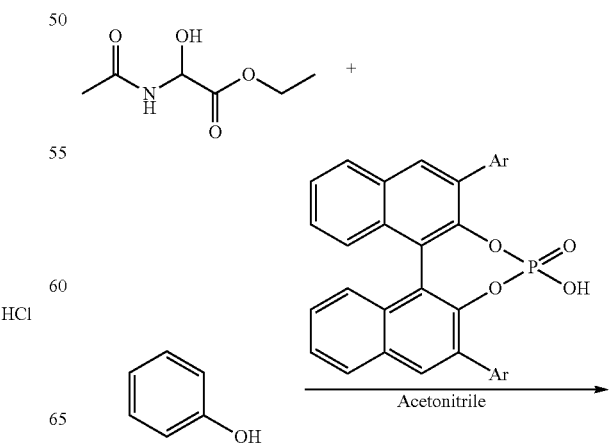

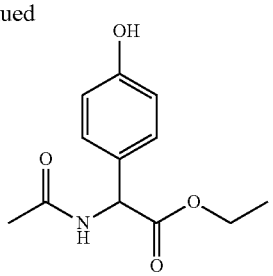

Specific operational steps are as follows:

Ethyl 2-acetamido-2-hydroxyacetate (1.932 g, 12 mmol), 0.1 mmol catalyst chiral phosphoric acid (wherein Ar is selected from the group consisting of hydrogen, phenyl, 2,4, 6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), phenol (0.94 g, 10 mmol), 50 mL acetonitrile were added sequentially into a 100 mL three-necked bottle equipped with a constant pressure dropping funnel and a thermometer, and the reaction solution was reacted at 81° C. for 34 hours, 1.47 g para-product was purified through after-treatment, yield 62%, melting point: 147-148° C., ee=90%. (HPLC conditions: chiralPAK AD-H 5 μm, 4.6×250 mm chromatographic column, n-hexane/isopropanol=9:1 was the mobile phase, the flow rate was 1.0 mL/min, the maximum absorption wavelength was 229 nm).

$^1$H NMR [400 MHz, CDCl$_3$]: δ 7.17 (d, J=8.4 Hz, 2H), 6.73 (d, J=8.4 Hz, 2H), 6.58 (d, J=6.4 Hz, 1H), 5.47 (d, J=6.8 Hz, 1H), 4.27-4.10 (m, 2H), 2.04 (s, 3H), 1.21 (t, J=7.2 Hz, 3H); $^{13}$C NMR [100 MHz, CDCl$_3$]: δ 171.4, 170.0, 156.5, 128.7, 128.4, 116.1, 62.2, 56.3, 23.4, 14.2.

Synthesis of levorotatory p-hydroxyphenylglycine hydrochloride, the synthetic route is shown as follows:

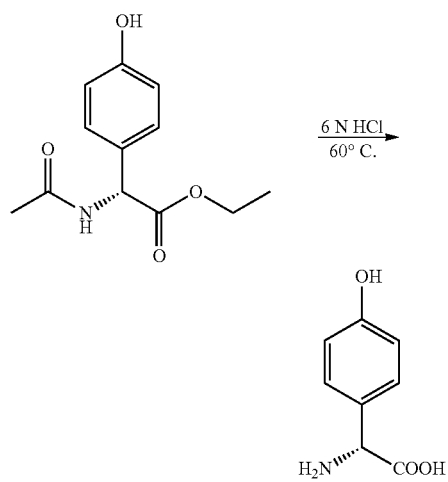

Specific operational steps are as follows:

99.3 mg D-ethyl-2-acetamido-2-(4-hydroxyphenyl)acetate (0.42 mmol), 2 mL 6N hydrochloric acid were sequentially added into a 10 mL schlenk tube, and started to stir, and reacted at 60° C. for 45 h, then the reaction was terminated, the reaction solution was rotary-dried, to obtain 66.8 mg while solid, the yield was 95%. [α]$_D^{20}$=−99.7° (c=1.0, water).

$^1$H NMR [400 MHz, D$_2$O]: δ7.35 (d, J=8.8 Hz, 2H), 6.96 (d, J=8.8 Hz, 2H), 5.09 (s, 1H); $^{13}$C NMR [100 MHz, D$_2$O]: δ 171.3, 157.1, 129.8, 123.4, 116.3, 56.2.

Example 7

Synthesis of ethyl 2-acetamido-2-hydroxyacetate, the synthetic route is shown as follows:

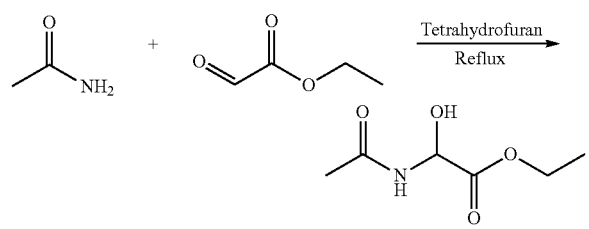

Specific operational steps are as follows:

Acetamide (1.47 g, 25 mmol), ethyl glyoxalate (50% solution in toluene, 5.35 g, 26.25 mmol), 20 mL tetrahydrofuran were added sequentially into a 50 mL eggplant-shaped flask. And they were reacted under reflux at 65° C. for 45 h, then cooled to a temperature of 25° C., plenty of white precipitate was precipitated, filtered by suction, and vacuum-dried at 45° C. for 11 h. 1.85 g white solid was obtained, and the molar yield was 47.13%.

$^1$HNMR [400 MHz, CDCl$_3$]: δ 6.83 (s, 1H), 5.65-5.50 (m, 1H), 4.45-4.21 (m, 3H), 2.05 (s, 3H), 1.33 (t, J=7.2 Hz, 3H).

Synthesis of D-ethyl-2-acetamido-2-(4-hydroxyphenyl) acetate, the synthetic route is shown as follows:

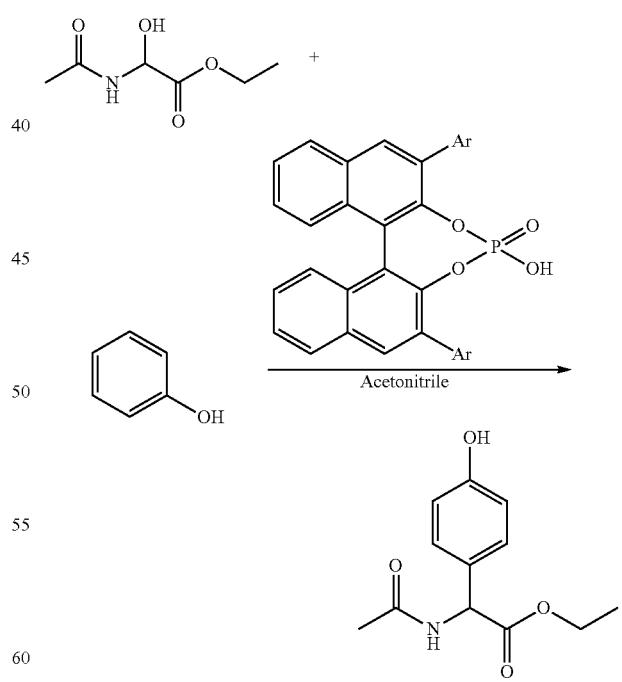

Specific operational steps are as follows:

Ethyl 2-acetamido-2-hydroxyacetate (1.932 g, 12 mmol), 0.1 mmol catalyst chiral phosphoric acid (wherein Ar is selected from the group consisting of hydrogen, phenyl, 2,4, 6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), phenol (0.94 g, 10 mmol), 50 mL acetonitrile were added sequentially into a 100 mL three-necked bottle equipped with a constant pressure dropping funnel and a thermometer, and the reaction solution was reacted at 81° C. for 34 hours, 1.67 g para-product was purified through after-treatment, yield 62%, melting point: 147-148° C., ee=90%. (HPLC conditions: chiralPAK AD-H 5 μm, 4.6×250 mm chromatographic column, n-hexane/isopropanol=9:1 was the mobile phase, the flow rate was 1.0 mL/min, and the maximum absorption wavelength was 229 nm).

$^1$H NMR [400 MHz, CDCl$_3$]: δ 7.17 (d, J=8.4 Hz, 2H), 6.73 (d, J=8.4 Hz, 2H), 6.58 (d, J=6.4 Hz, 1H), 5.47 (d, J=6.8 Hz, 1H), 4.27-4.10 (m, 2H), 2.04 (s, 3H), 1.21 (t, J=7.2 Hz, 3H); $^{13}$C NMR [100 MHz, CDCl$_3$]: δ 171.4, 170.0, 156.5, 128.7, 128.4, 116.1, 62.2, 56.3, 23.4, 14.2.

Synthesis of levorotatory p-hydroxyphenylglycine, the synthetic route is shown as follows:

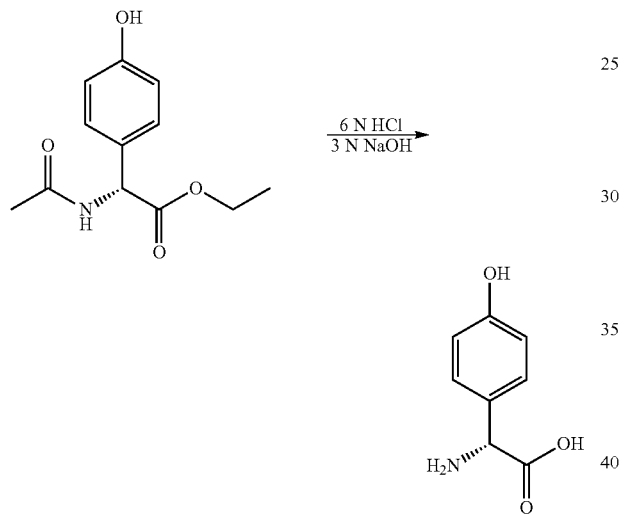

Specific operational steps are as follows:

0.807 g D-ethyl-2-acetamido-2-(4-hydroxyphenyl)acetate (3.4 mmol), 12 mL 6 N hydrochloric acid were sequentially added into a 25 mL eggplant-shaped flask, and started to stir, reacted at 60° C. for 14 hours and 40 minutes, then the reaction was terminated, the reaction solution was rotary-dried, and the pH was adjusted to 5.5 with 3N sodium hydroxide, to obtain 0.245 g white solid, yield 43.2%. [c]$_D^{20}$=−156.6° (c=1.0, 1 N hydrochloric acid). $^1$H NMR [400 MHz, D$_2$O]: δ7.20 (d, J=8.4 Hz, 2H), 6.81 (d, J=8.4 Hz, 2H), 5.00 (s, 1H).

Example 8

Synthesis of ethyl 2-acetamido-2-hydroxyacetate, the synthetic route is shown as follows:

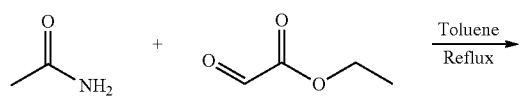

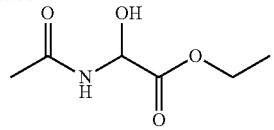

Specific operational steps are as follows:

Acetamide (1.47 g, 25 mmol), ethyl glyoxalate (50% solution in toluene, 2.55 g, 12.5 mmol), 20 mL toluene were added sequentially into a 50 mL eggplant-shaped flask. And they were reacted at 110.6° C. for 30 min, cooled to 20° C., and plenty of white precipitate was precipitated, filtered by suction, and vacuum-dried at 50° C. for 6 h. 1.73 g white solid was obtained, and the molar yield was 85.76%.

$^1$HNMR [400 MHz, CDCl$_3$]: δ 7.30 (d, J=6.8 Hz, 1H), 5.58 (d, J=7.6 Hz, 1H), 5.40 (s, 1H), 4.27-4.21 (q, J=7.2 Hz 2H), 2.02 (s, 3H), 1.29 (t, J=7.2 Hz, 3H).

Synthesis of D-ethyl-2-acetamido-2-(4-hydroxyphenyl)acetate, the synthetic route is shown as follows:

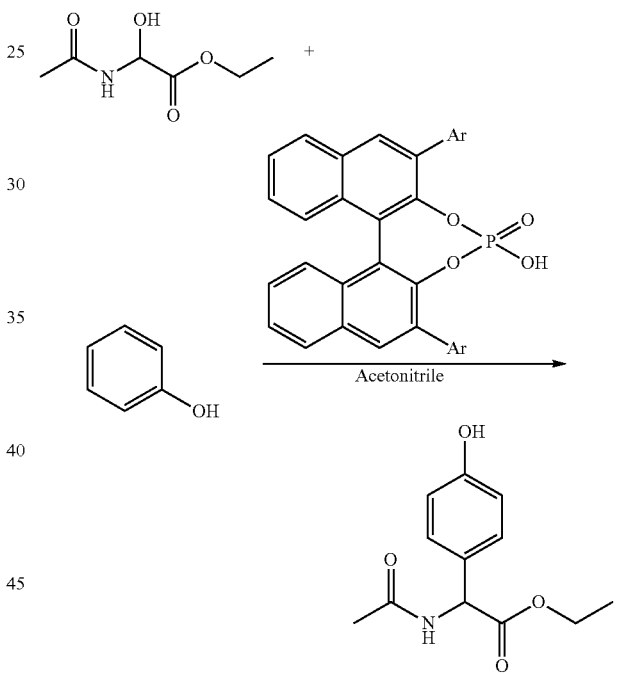

Specific operational steps are as follows:

Ethyl 2-acetamido-2-hydroxyacetate (1.932 g, 12 mmol), 0.1 mmol catalyst chiral phosphoric acid (wherein Ar is selected from the group consisting of hydrogen, phenyl, 2,4,6-triisopropylphenyl, 3,5-bis(trifluoromethyl)phenyl, β-naphthyl, triphenylsilyl, 9-anthryl, 4-biphenylyl, 4-nitrophenyl, 9-phenanthryl, 4-methoxyphenyl, and 4-nitrophenyl), phenol (0.94 g, 10 mmol), 50 mL acetonitrile were added sequentially into a 100 mL three-necked bottle equipped with a constant pressure dropping funnel and a thermometer, and the reaction solution was reacted at 81° C. for 34 hours, 1.47 g para-product was purified through after-treatment, yield 62%, melting point: 147-148° C., ee=90%. (HPLC conditions: chiralPAK AD-H 5 μm, 4.6×250 mm chromatographic column, n-hexane/isopropanol=9:1 was the mobile phase, the flow rate was 1.0 mL/min, the maximum absorption wavelength was 229 nm).

$^1$H NMR [400 MHz, CDCl$_3$]: δ 7.17 (d, J=8.4 Hz, 2H), 6.73 (d, J=8.4 Hz, 2H), 6.58 (d, J=6.4 Hz, 1H), 5.47 (d, J=6.8 Hz, 1H), 4.27-4.10 (m, 2H), 2.04 (s, 3H), 1.21 (t, J=7.2 Hz, 3H); $^{13}$C NMR [100 MHz, CDCl$_3$]: δ 171.4, 170.0, 156.5, 128.7, 128.4, 116.1, 62.2, 56.3, 23.4, 14.2.

Synthesis of levorotatory p-hydroxyphenylglycine hydrochloride, the synthetic route is shown as follows:

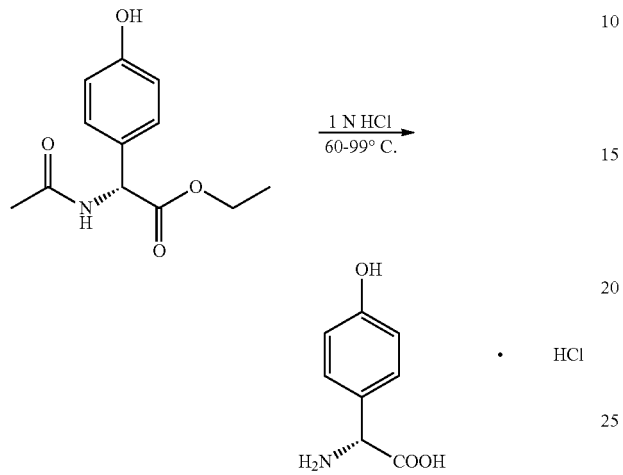

Specific operational steps are as follows:

99.6 mg D-ethyl-2-acetamido-2-(4-hydroxyphenyl)acetate (0.42 mmol), 2 mL IN hydrochloric acid were sequentially added into a 10 mL schlenk tube, and started to stir, and reacted at 60° C. for 45 h, heated to 80° C. and reacted for 13.5 h, then heated to 99° C. and reacted for 11 h, then the reaction was terminated, the reaction solution was rotary-dried, to obtain 70.0 mg while solid, the yield was 99%. [α]$_D^{20}$=−85° (c=1.0, water).

$^1$H NMR [400 MHz, D$_2$O]: δ7.34 (d, J=8.8 Hz, 2H), 6.95 (d, J=8.4 Hz, 2H), 5.06 (s, 1H).

The method of synthesizing levorotatory p-hydroxyphenylglycine compounds provided by the present invention is described above in detail. Specific examples are employed herein to illustrate the principles and embodiments of the present invention, and the above examples are only described to facilitate the understanding of the method and the core idea of the present invention. It should be noted that, a number of additional alterations and modifications can be made to the present invention by a skilled in the art, without departing from the principle of the present invention, these alterations and modifications also fall within the protection scope of the claims of the present invention.

The invention claimed is:

1. A method of synthesizing levorotatory p-hydroxyphenylglycine compounds, characterized in that, the method comprises the following steps:
    step 1: the compound of formula II and the compound of formula III undergo nucleophilic addition reaction in a first solvent, to produce the compound of formula IV;
    wherein the first solvent is selected from the group consisting of ether solvent, ester solvent, haloalkane solvent, C$_5$~C$_{10}$ hydrocarbon solvent, nitrile solvent, and ketone solvent;
    step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, C$_5$-C$_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, and chiral phosphoric acid, and the achiral acid is selected from the group consisting of methanesulfonic acid, p-toluenesulfonic acid, trifluoromethanesulfonic acid, sulfuric acid, and hydrochloric acid;

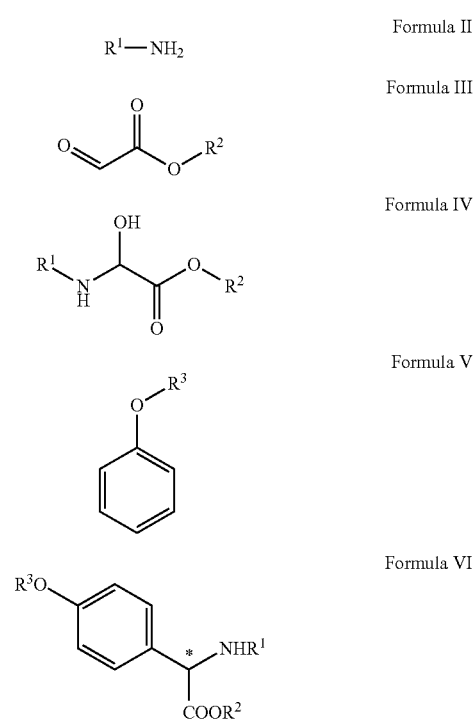

wherein, R$^1$ is selected from the group consisting of acetyl, benzoyl, tert-butoxycarbonyl, benzyloxycarbonyl, formamido, and pivalyl; R$^2$ is selected from the group consisting of methyl, ethyl, isopropyl, tert-butyl, and benzyl; and R$^3$ is selected from the group consisting of hydrogen, methyl, trimethylsilyl, tert-butyldimethylsily, and triisopropylsilyl.

2. The method according to claim 1, characterized in that, in step 1, the molar ratio of the compound of formula II to the compound of formula III is 1:0.5~1:2.1.

3. The method according to claim 1, characterized in that, in step 1, the nucleophilic addition reaction is carried out at a temperature of 25~110.6° C. for a period of 0.5~144 h.

4. The method according to claim 1, characterized in that, in step 2, the molar ratio of the compound of formula IV to the compound of formula V is 1:0.2~1:5.

5. The method according to claim 1, characterized in that, in step 2, the molar ratio of the compound of formula IV or the compound of formula V to the catalyst is 1~200:1.

6. The method according to claim 1, characterized in that, in step 2, the Friedel-Crafts-like reaction is carried out at a temperature of 40~82° C. for a period of 13.5-96 h.

7. A method of synthesizing a levorotatory p-hydroxyphenylglycine having the structure of formula I,

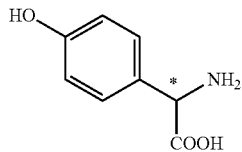

Formula I characterized in that, the method comprises the following steps:

step 1: the compound of formula II and the compound of formula III undergo nucleophilic addition reaction in a first solvent, to produce the compound of formula IV; wherein the first solvent is selected from the group consisting of ether solvent, ester solvent, haloalkane solvent, $C_5$~$C_{10}$ hydrocarbon solvent, nitrile solvent, and ketone solvent;

step 2: the compound of formula IV and the compound of formula V undergo a Friedel-Crafts-like reaction in a second solvent, using acid as catalyst, to produce the levorotatory p-hydroxyphenylglycine compound having the structure of formula VI; wherein the second solvent is selected from the group consisting of nitrile solvent, haloalkane solvent, $C_5$-$C_{10}$ hydrocarbon solvent; the acid is a chiral acid or an achiral acid, wherein the chiral acid is selected from the group consisting of D-tartaric acid, L-tartaric acid, D-camphorsulfonic acid, L-camphorsulfonic acid, L-proline, D-proline, and chiral phosphoric acid, and the achiral acid is selected from the group consisting of methanesulfonic acid, p-toluenesulfonic acid, trifluoromethanesulfonic acid, sulfuric acid, and hydrochloric acid;

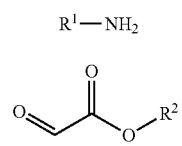

Formula II

Formula III wherein, $R^1$ is selected from the group consisting of acetyl, benzoyl, tert-butoxycarbonyl, benzyloxycarbonyl, formamido, and pivalyl; $R^2$ is selected from the group consisting of methyl, ethyl, isopropyl, tert-butyl, and benzyl; and $R^3$ is hydrogen;

step 3: in a mixed solution of alcohol and water, or in water, the compound of formula VI undergoes hydrolysis reaction by adjusting the pH value to be <2, then the solution is neutralized with a base to a pH value of 5.2~5.6, to obtain the compound of formula I.

8. The method according to claim 7, characterized in that, in step 3, the hydrolysis reaction is carried out at a temperature of 60~100° C.

9. The method according to claim 7, characterized in that, in step 3, the acid is selected from the group consisting of hydrochloric acid, sulfuric acid, methanesulfonic acid, and trifluoromethanesulfonic acid.

10. The method according to claim 7, characterized in that, in step 3, the base is selected from the group consisting of sodium hydroxide, sodium bicarbonate, sodium carbonate, potassium hydroxide, and aqueous ammonia.

* * * * *